United States Patent [19]

Deisenroth et al.

[11] Patent Number: 5,585,517
[45] Date of Patent: Dec. 17, 1996

[54] PROCESS FOR REACTING A PERFLUOROALKL IODIDE WITH AN OLEFINIC COMPOUND

[75] Inventors: Ted Deisenroth, Carmel; Robert Falk, New City, both of N.Y.; Juerg Haase, Riehen, Switzerland

[73] Assignee: Ciba-Geigy Corporation, Tarrytown, N.Y.

[21] Appl. No.: 420,386

[22] Filed: Apr. 12, 1995

Related U.S. Application Data

[63] Continuation-in-part of Ser. No. 270,068, Jul. 1, 1994, abandoned.

[51] Int. Cl.$^6$ .................................................. C07C 59/295
[52] U.S. Cl. ........................... 562/583; 562/588; 562/595; 570/135
[58] Field of Search .................................. 562/583, 588, 562/595; 570/135

[56] References Cited

U.S. PATENT DOCUMENTS

| | | | |
|---|---|---|---|
| 3,257,407 | 6/1966 | Brace | 260/290 |
| 4,058,573 | 11/1977 | Knell | 260/653.1 |
| 4,387,254 | 6/1983 | Commeyras | 568/842 |

FOREIGN PATENT DOCUMENTS

| | | |
|---|---|---|
| 0194348 | 9/1986 | European Pat. Off. . |
| 438166 | 7/1991 | European Pat. Off. . |

OTHER PUBLICATIONS

Journal of Fluorine Chemistry, 58(1992) pp. 1–8, Huang, "Perfluoroalkylation initiated with sodium dithionite and related systems".
Chem. Abst 116(9), 82914b (1992).
Chem. Abst. 115(1), 8053h (1991).
Chem. Abst. 106(11), 83935q (1987).

*Primary Examiner*—Paul J. Killos
*Assistant Examiner*—Dwayne C. Jones
*Attorney, Agent, or Firm*—Kevin T. Mansfield

[57] ABSTRACT

A novel process is described for reacting a perfluoroalkyl iodide with an olefinic compound, which comprises carrying out a free-radical addition reaction of the perfluoroalkyl iodide to the olefin in the presence of azoic or peroxy initiator and a water-soluble salt selected from the group consisting of sulfites, bisulfites, metabisulfites and dithionites. The adducts are obtained in high yield and purity and are useful for the preparation of oil- and water repellent products for use on paper, textiles, metal, wood and the like, or as precursors for fluorinated surfactants.

22 Claims, No Drawings

PROCESS FOR REACTING A PERFLUOROALKL IODIDE WITH AN OLEFINIC COMPOUND

This application is a continuation-in-part of application Ser. No. 08/270,068 filed on Jul. 1, 1994, abandoned on Apr. 18, 1995.

BACKGROUND AND RELATED PRIOR ART

The present invention relates to an improved process for reacting a perfluoroalkyl iodide with an olefinic compound.

The free radical chain addition of perfluoroalkyl iodides ($R_FI$) to olefinic groups has long been known. Free-radical addition to allyl compounds initiated by azoic initiators is described for example in U.S. Pat. Nos. 3,083,224, 3,145, 222 and 3,257,407. However the yields are low. Attempts to improve the process included the use of amines and amine salts and of copper ions (French Pat. No. 2,103,459), but this did not result in substantial improvements in yield. In U.S. Pat. No. 4,387,254 a 100% conversion of $R_FI$ to the adduct is achieved using a 5-molar excess of allyl alcohol, mercurous or mercuric iodide as catalyst and dimethylformamide as solvent, making the process unacceptable for environmental reasons.

In European Patent Application EP 0,483,166 the synthesis of certain $R_FI$/allyl alcohol addition products in high yield is described. The reaction is carried out in the presence of water, basic compounds, metal oxides, silver compounds or epoxy compounds and using 1% by weight azo-bis-isobutyronitrile (AIBN) as initiator. The amount of water to use ranges from 0.1 to 5 times the amount of $R_FI$, but is preferably not more than equal in weight. However when this process is used for the addition of $R_FI$ to larger unsaturated molecules and especially to alcohols and diols containing more than 1 allyl group, as for instance described in copending patent application Ser. No. 08/270,083 now U.S. Pat. No. 5,991,261 issued on Feb. 13, 1995, yields are too low and the reaction rates are too slow to be practical.

By elimination of HI from the $R_FI$ olefin-adducts by treatment with a base, $R_F$-substituted alkylenes are formed which are useful, either by themselves or as intermediates, as oil-and water repellent finishes for a wide variety of substrates such as textiles, paper, leather, wood, masonry, glass or metal.

SUMMARY OF THE INVENTION

It has now been discovered that if the free radical addition of a perfluoroalkyl iodide ($R_FI$) to an olefinically unsaturated compound is carried out in the presence of an azoic or peroxy initiator and a water-soluble salt or salts selected from the group consisting of sulfites, bisulfites, metabisulfites and dithionites, the amount of initiator necessary can be reduced by at least 50%, while at the same time the reaction rate, yield and purity of the desired addition product are substantially improved. This is especially true for the addition of $R_FI$ to allyl alcohol and to compounds with more than one olefinic group as well as for other compounds which, using the reaction conditions of the prior art, are slow to react. Such compounds are for example described in copending U.S. patent application Ser. No. 08/270,083 now U.S. Pat. No. 5,491,261. It is especially important for making higher performance oil-repellent paper sizes and textile finishes that the addition of $R_FI$ to bis-olefins be essentially quantitative, because mono-adducts do not perform well, either as ionic paper sizes or as building blocks for polyurethanes.

DETAILED DESCRIPTION

The process of the invention comprises carrying out a free-radical addition reaction of the perfluoroalkyl iodide to the olefinic compound in the presence of an azoic or peroxyinitiator and an aqueous solution of a water-soluble salt selected from the group consisting of sulfites, bisulfites, metabisulfites and dithionites.

The symbol $R_F$ denotes a perfluoroalkyl group of the formula $C_nF_{2n+1}$, wherein n is an integer from 4 to 20, preferably from 6 to 14. The reactant $R_FI$ can be a pure compound but, more typically, consists of a mixture of homologues with different $R_F$-chain lengths. Such compounds are known per sè and can be prepared by known methods.

The water-soluble salt is a alkali metal or ammonium salt of the class of sulfite, bisulfite, metabisulfite or dithionites, and is used in amounts ranging from 0.01–30 mole percent based on $R_FI$, preferably from 0.5 to 5 mole percent. Preferably the cation is sodium or potassium and the anion is sulfite or bisulfite.

Olefinic compounds useful in the practice of this invention contain one or more olefinic groups, preferably terminal olefinic groups. The olefinic compound preferably is substituted by one or more than one functional groups, which may be the same or different, such as hydroxy, carboxy, unsubstituted amino or amino which is mono- or disubstituted by $C_1$–$C_5$alkyl or hydroxy- or carboxy-substituted $C_1$–$C_5$alkyl, amide, $C_1$–$C_4$alkyl-substituted amide, or anhydride groups. The olefinic compound can also contain one or more than one heteroatom-containing group such as an ether, sulfide, sulfone, ester, amide or tertiary amino groups. Said compounds are known per se and are generally commercially available.

Typical olefinic compounds useful in the practice of this invention include hydrocarbons such as 1-pentene, cyclopentadiene and norbornene. Typical examples of unsaturated alcohols include allyl alcohol, methallyl alcohol, crotyl alcohol, 3-methyl-3-butene-1-ol, 1-butene-3-ol, 3-butene-1-ol, 1,4-butenediol, ω-unsaturated alkenols such as dodecane-1-ol-11,12-ene, decane-1-ol-9, 10-ene, trimethylolpropane diallylether, pentaerythritol mono-, di-, and triallylether, compounds of the formulae

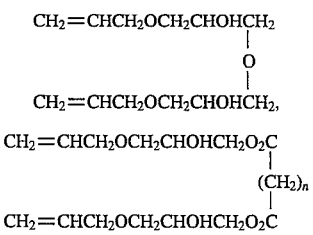

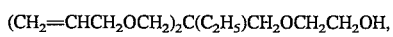

where n=1–4,

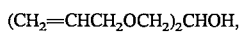

(CH$_2$=CHCH$_2$OCH$_2$)$_2$CHOH,

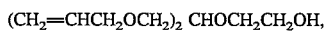

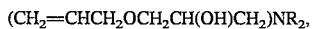

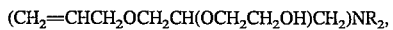

wherein $R_2$ is $C_1$–$C_5$alkyl or hydroxy- or carboxy-substituted $C_1$–$C_5$alkyl, $(CH_2=CHCH_2OCH_2CH(OH)CH_2)_2S$, $(CH_2=CHCH_2OCH_2CH(OCH_2CH_2OH)CH_2)_2S$, $(CH_2=CHCH_2OCH_2CHOH)_2$, oligomers of allyl glycidyl ether and adducts of allyl glycidyl ether with active hydrogen compounds such as alcohols, amines and mercaptans, including amino acids, amino alcohols, mercapto acids and mercapto alcohols.

Examples of suitable unsaturated acids include:

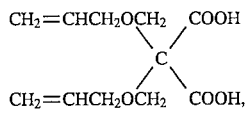

$CH_2=CHCH_2OCH_2$
$|$
$CH_2=CHCH_2OCH-COOH$, $CH_2=CHCH_2OCOCH-COOH$
$|$
$CH_2=CHCH_2OCOCH-COOH$, $H_3C-C(COOH)-(CH_2OCH_2-CH=CH_2)_2$, $(CH_2=CHCH_2OCH_2CH(OH)CH_2)_2N-C(COOH)CH_2COOH$, $H_3C-C(COOH)-(CH_2O_2COCH_2-CH=CH_2)_2$ and

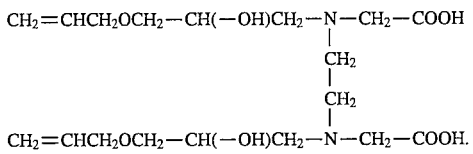

The corresponding $R_FI$ addition products of the above-mentioned compounds are described in copending U.S. patent application Ser. No. 08/270,083 now U.S. Pat. No. 5,491,261. Also of interest are $R_FI$ addition products of polyunsaturated compounds such as 1,4- and 1,2-polybutadienes of 200 to 5000 molecular weight, especially those terminated with hydroxy or carboxy groups.

Also of interest are $R_FI$ addition products of monounsaturated acids, anhydrides and alcohols, for example ω-alkylenic acids and alcohols such as 10-undecenoic acid and 10-undecen-1-ol, norbornene derivatives such as norbornene- and methylnorbornene dicarboxylic acids and their corresponding anhydrides, allylsuccinic acid and its anhydride, itaconic acid and its anhydride, vinyl ether derivatives such as hydroxybutylvinyl ether, and allyl glycidyl ether.

The elimination of HI from the $R_FI$-adducts of the above compounds with a base gives products useful, directly or after conversion to sulfate or phosphate esters, as oil- and water repellent paper sizes, as described for instance in copending patent application Ser. No. 08/270,083 now U.S. Pat. No. 5,491,261. Especially useful products for this use are 11-$R_F$-10-undecylenic acid, 11-$R_F$-10-undecylenyl sulfate, mono- and di- 11-$R_F$-10-undecylenyl phosphate, 3-$R_F$-2-propenyl succinic acid and 3-$R_F$-itaconic acid.

Preferred olefinic compounds for use in this invention are allyl alcohol, pentaerythritol di-and triallyl ether, trimethylolpropane diallyl ether, glycerol-1,3-diallyl ether, allyl glycidyl ether, oligomers of allyl glycidyl ether, adducts of allyl glycidyl ether with amino acids and alcohols and mercapto acids and alcohols, as well as 10-undecenoic acid and 10-undecen-1-ol.

The reaction of the perfluoroalkyliodide with the olefin is carried out in the presence of a free radical-generating initiator at a temperature of from about 50° to 120° C., preferably from 50° to 90° C. Any type of common initiator, such as a peroxide or bisazo compound, can be used which has a practical decomposition rate at the indicated temperature ranges. Suitable peroxides include benzoyl peroxide, lauroyl peroxide, tert. butyl peroctoate and di-tert. butyl peroxide.

The preferred initiators are azo compounds. Preferred azo compounds are azobis(isobutyronitrile), azobis(isovaleronitrile) and azobis(cyclohexane carbonitrile).

The amount of initiator can vary, depending on reaction conditions and the nature of the unsaturated reactant, from 0.01 to 3 mole percent of $R_FI$. Preferred initiator concentrations are from 0.5%–2 mole percent.

The addition reaction can be carried out either in bulk or in the presence of a suitable organic solvent which is inert to the reactants and volatile enough to be recovered by distillation, including vacuum distillation if necessary. Suitable organic solvents include alcohols, ketones, esters, amides, hydrocarbons and mixtures thereof. Examples of suitable solvents are methanol, ethanol, isopropanol, butanol, acetone, methyl ethyl ketone, methyl propyl ketone, isopropyl acetate, N-methylpyrrolidone, toluene and xylene.

The sulfite or dithionite salt is added as an aqueous solution and forms a separate phase. Intensive stirring is required to achieve good mixing. The weight ratio of the aqueous solution of the water-soluble salt to the non-aqueous phase comprising the perfluoroalkyl iodide, the olefinic compound and the organic solvent, if one is used, can range from 0.05 to 10 and is preferably 0.1 to 0.5. Within the disclosed ratios the amount of water is not critical, but it is preferably sufficient to dissolve the salt. It is often advantageous to add one of the reactants, preferably the olefinic compound, continuously over a period of several hours in order to control the exotherm.

In addition to speeding up the reaction by reducing any free iodine, the sulfite or thionate salts help to salt out water-soluble reactants like allyl alcohol. This latter effect can also be achieved by adding non-reactive common water-soluble salts such as sodium or potassium chloride or sulfate to the reaction mixture.

The process of this invention is illustrated in greater detail in the following non-limiting examples.

EXAMPLE 1

1000 g (1.79 mol) of a perfluoroalkyl iodide ($R_FI$) with a $R_F$-chain length distribution of $C_6/C_8/C_{10}/C_{12}/C_{14}/C_{16}$ of 32/31/19/10/4.7/2% by weight (Telomer-A, from DuPont) is charged into a 2 l flask equipped with stirrer, condenser and $N_2$-inlet tube and heated to 75° C. under a nitrogen blanket with stirring. Then 333.3 g of water is added with vigorous stirring, together with 106 g (0.56 mol) of sodium metabisulfites ($Na_2S_2O_5$). After the mixture turns colorless, 155.7 g (2.68 mol) of allyl alcohol is added, followed by 10.4 g (0.054 mol) 2,2'-azobis(2-methylbutyronitrile) (VAZO-67, from WAKO Chem. Co.). An immediate 25° C. exotherm is observed. The mixture is cooled back to 75° C. and maintained at this temperature for 3 hours. Samples am taken every 30 minutes and analysed by gas chromatography for conversion of $R_FI$. After 30 minutes, the conversion to product is essentially 100%. Then 220 g methyl propyl ketone is added and the mixture is allowed to separate, whereupon the top aqueous layer is sucked off. The remaining product layer is washed at 90° C. with 400 g of deionized water and the remaining solvent is removed by vacuum distillation. The product is isolated as a melt.

EXAMPLE 2

The process of example 1 is repeated, but without using $Na_2S_2O_5$. No exotherm is observed and the conversion of $R_FI$ after 30 minutes is 21%, after 1 hour 57% and reaches 100% only after 3 hours.

EXAMPLE 3

Alternate process for making 3-perfluoroalkyl-2-iodopropanol. Into a 1l round-bottom-flask equipped with condenser, thermometer, stirrer and a nitrogen gas inlet tube are charged 606.0 g (1.0 mole) of a perfluoroalkyl iodide ($R_FI$) with a homologue distribution of 1.7% $C_6$, 49.8% $C_8$, 33.5% $C_{10}$, 11.1% $C_2$, 3.1% $C_{14}$, 0.69% $C_{16}$ and 0.16% $C_8$, (Telomer-AN, from DuPont), 22.6 g $H_2O$ (1.26 mole) and 14.8 g sodium metabisulfite ($Na_2S_{2O5}$, 0.078 mole). The mixture is heated on an oil bath to 80° C. with stirring. After the addition of 2.88 g (0.015 mole) 2,2'-azobis(2-methylbutyronitrile) (VAZO-67, from WAKO Chem. Co.), 112.8 g allyl alcohol (1.16 mole) as a 60% solution in water is continuously added over 210 minutes using a Masterflex pump at a flow rate of 32.2 g/h. A small temperature increase of the reaction mass is observed. Product formation is followed by monitoring the decrease of $R_FI$ concentration via gas chromatography. No substantial accumulation of $R_FI$ is seen, i.e. the allyl alcohol reacts immediately upon addition. After 210 minutes, the addition rate of the aqueous allyl alcohol solution addition is increased to 102 g/h for the following two hours. The total amount of allyl alcohol solution used in the reaction is 318.2 g, corresponding to a molar ratio of $R_FI$ to allyl alcohol of 1.0:3.28. The total amount of water used is 31.5%, based on $R_FI$.

The $R_F$-iodohydrin product is obtained as a solution in the excess allyl alcohol. The excess allyl alcohol is distilled off in vacuo and the product is filtered off, rinsed with deionized water and dried in vacuo at 50° C. It is obtained as a dark yellow waxy solid in 98% yield; the conversion of $R_FI$ is 100%.

EXAMPLE 4

The process of Example 3 is repeated, but without using sodium metabisulfite ($Na_2S_2O_5$). After the allyl alcohol addition is complete, conversion of $R_FI$ is only 88%, and, after 4 more hours at 80° C., only 92%.

EXAMPLE 5

The process of example 3 is repeated with the following changes: 45.2 g water are added initially, 5.0 g VAZO-67 are used and 63.9 g (1.1 moles) allyl alcohol (100%) are added uniformly at a rate of 21.3 g/h. The total amount of water used is 7.5%, based on $R_FI$.

After 5 hours of reaction time, the conversion of $R_FI$ is 99%.

EXAMPLE 6

The process of Example 5 is repeated, but without using sodium metabisulfite ($Na_2S_2O_5$). After the same procedure is carried out, conversion of $R_FI$ is only 83.3%.

EXAMPLE 7

The process of example 5 is repeated using the following charges: 606 g (1.0 mol) $R_FI$ (Telomer-AN from DuPont), 45.2 g water, 14.8 g (0.078 moles) $Na_2S_2O_5$, 5.0 g (0.02 moles) 2,2'-azobis(2,4-dimethylpentanenitrile) (VAZO-52) and 63.9 g (1.1 moles) allyl alcohol. After a 5 hour reaction time, conversion of $R_FI$ is 97.2%.

EXAMPLE 8

The process of Example 7 is repeated, but without using sodium metabisulfite ($Na_2S_2O_5$). After the same procedure is carried out, conversion of $R_FI$ is only 54%.

EXAMPLE 9

Into a 4 oz. bottle equipped with magnetic stirrer and a rubber septum are placed 15 g (0.0271 tool) $R_FI$ with a $R_F$-chain length distribution of $C_6/C_8/C_{10}/C_{12}/C_{14}/C_{16}$ of 32/31/19/10/4.7/2% by weight (Telomer-A, from DuPont), 1.54 g (0.0051 mol) of sodium metabisulfite and 4.95 g distilled water. This mixture is heated to 70° C. Its color changes from purple to colorless. Then 6.09 g (0.0284 mol) of trimethylolpropane diallyl ether are added to this mixture along with 0.156 g (0.0005 tool) 2,2'-azobis(2-methylbutyronitrile) (VAZO-67). The mixture is purged with nitrogen, sealed and placed in the heating bath set at a constant temperature of 70° C. The reaction's progress is monitored by following the disappearance of $R_FI$ and the appearance of product, using gas chromatography. After 5 hours the amount of $R_FI$ remaining is 0.4%. The product is a clear gel-like mixture at 70° C.

EXAMPLES 10–12

Following the procedure of example 9, identical reactions are carried out using, instead of sodium metabisulfite; sodium sulfite, sodium dithionite and water alone as a control.

The table below shows the conversions of $R_FI$ at 1 hour time intervals.

| Example # | Additive | % $R_FI$ Conversion, after hours | | |
| --- | --- | --- | --- | --- |
| | | 1 | 2 | 3 |
| 9 | Na metabisulfite | 89 | 98 | 99 |
| 10 | Na sulfite | 98 | 100 | 100 |
| 11 | Na dithionite | 97 | 98 | 100 |
| 12 | water only | 49 | 85 | 89 |

EXAMPLE 13

Into a 100 ml 3-necked round-bottom flask equipped with stirrer, condenser, gas inlet tube and thermometer are placed 45.74 g (0.0756 moles) of $R_FI$ with a $R_F$-chain length distribution of 1.7% $C_6$, 49.8% $C_8$, 33.5% $C_{10}$, 11.1% $C_{12}$, 3.1% $C_{14}$, 0.69% $C_{16}$ and $C_{18}$, (Telomer-AN, from DuPont), 23.23 g distilled water, and 15.27 g (0.0829 moles) 10-undecylenic acid. The mixture is stirred and sparged with nitrogen and 1 g dry ice, then heated to 80° C. Then 0.0239 g (0.13 mmoles) 2,2'-azobis(2-methylbutyronitrile) (VAZO-67) are added, followed by 0.0261 g VAZO-67 after 3 hours and 0,0331 g VAZO-67 after 7 hours. The progress of the reaction is monitored by observing the disappearance of $R_FI$ by gas chromatography.

EXAMPLE 14

Example 13 is repeated in the presence of 5 mole % sodium metabisulfite using 47.25 g (0.0781 moles) $R_F$-iodide, 0.75 g (0.004 moles) sodium metabisulfite, 24.03 g distilled water and 15.79 g (0.0857 moles) 10-undecylenic acid. The tool ratio of $R_FI$ to 10-undecylenic acid is 1/1.1. The initial dosage of VAZO-67 is 0.0258 g (0.13 mmoles). After 3 hours 0.0274 g VAZO-67 and after 7 hours 0.0381 g VAZO-67 are added. The extent of reaction in this and the previous example is shown below.

| Conversion of $R_fI$ after | 4 hours | 9 hours |
|---|---|---|
| Example 13 | 60.5 | 78.4 |
| Example 14 | 67.6 | 94.8. |

EXAMPLE 15

Synthesis of 1-propanol,
3-(perfluoro-$C_{6-18}$alkyl-2-propenyl)-oxy)-
2,2-bis-((perfluoro$C_{6-18}$alkyl-2-propenyl)oxy)methyl)-

Into a 2000 ml glass reactor are charged 1394 g (2.32 mol) perfluoroalkyl iodide with a $R_f$-chain length distribution of 1.7% $C_6$, 49.8% $C_8$, 33.5% $C_{10}$, 11.1% $C_{12}$, 3.1% $C_{14}$, 0.69% $C_{16}$ and 0.16% $C_{18}$, (Telomer-AN, from DuPont), 200 g (0.78 tool) of the triallyl ether of pentaerytrerythritol (NEOALLYL T-30, DAISO CO., LTD)containing 15 weight di-allyl, 75% tri-allyl and 10% tetra-allyl ethers; 2.7 g (0.014 mol) azobis(isobutyronitdie) (AIBN), 1.2 g (0.116 mol) sodium bisulfite, 538 g deionized water and 311 g (3.89 mol) 50% NaOH. The temperature of the reaction mixture is increased to 85° C. and it is stirred vigorously. After 6 hours a second charge of 1.8 g (0.009 mol) of AIBN is made. After 18 hours the reaction is complete and the top aqueous layer is removed. The reaction mixture is washed with 269 g deionized water at 85° C., followed by a wash with 107.6 g of 5% HCl and a final wash with 269 g deionized water at 85° C. The product is isolated as a fatty yellow to white solid in a yield of 1249 g (95%), m.p. 72°–80° C. The product contains 73% of the trans isomer as determined from integration of the $^1$H-NMR spectrum. $^1$H-NMR of the trans isomer is consistent with that obtained from 1-propanol, 3-((4,4,5,5,6,6,7,7,8,8,9,9,10,10,11,11,11-heptadecafluoro-2-undecenyl)oxy)-2,2-bis (((4,4,5,5,6,6,7,7,8,8,9,9,10,10,11,11,11-heptadecafluoro-2-undecenyl)oxy)methyl)-.
$^1$H-NMR, cis isomer (500 MHz, CDCl$_3$), d 6.22 (bm, 3H, —CF$_2$C$\underline{H}$=CH—), 5.62 (dt, 3 H, —CF$_2$CH$_2$=C$\underline{H}_b$CH$_{2c}$—, $J_{a,b}$=13.7 Hz and $J_{a,c}$=15.4 Hz), 4.28 (bs, 6H, —CF$_2$CH=C$\underline{H}_2$O—), 3.72 (s, 2H, —C$\underline{H}_2$OH) and 3.53 (s, 6H, —OC$\underline{H}_2$C—).

EXAMPLE 16

The process of Example 1 is repeated, but without using the free radical initiator VAZO-67. The progress of the reaction is monitored by gas chromatography. Unreacted perfluoroalkyl iodide ($R_fI$) is quantified using an external standard technique. The results are as follows: at 30 minutes 14.95 mole % $R_fI$ consumed, at 60 minutes 59.71 mole % $R_fI$ consumed, at 90 minutes 82.90 mole % $R_fI$ consumed and at 21 hours only 93.52 mole % $R_fI$ consumed.

EXAMPLE 17

100 g (0.166 mole) of $R_fI$ with an $R_f$-chain length distribution of $C_6/C_8/C_{10}/C_{12}/C_{14}/C_{16}$ being 2.3/48.7/31.4/12.4/3.9/1.0/0.3/0.1% by weight respectively (Telomer-AN, from DuPont), is added to a 300 ml three neck round-bottomed flask along with 1.71 g (0.0090 mole) of Na$_2$S$_2$O$_5$, 18.6 g of deionized water and 9.6 g of propanol. This mixture is heated to 80° C. with stirring. At 80° C., 0.69 g (0.0036 mole) of VAZO-67 is added followed by 19.1 g (0.09 mole) of trimethylolpropane diallyl ether. The temperature of the reaction mixture is held constant at 80° C. The progress of the reaction is monitored by gas chromatography. Unreacted perfluoroalkyl iodide ($R_fI$) is quantified using an external standard technique. The results are as follows: at 30 minutes 99.0 mole % $R_fI$ consumed, at 60 minutes 99.1 mole % $R_fI$ consumed and at 240 minutes 99.1 mole % $R_fI$ consumed.

EXAMPLE 18

The process in Example 17 is repeated, but without using radical initiator VAZO-67. The progress of the reaction is monitored by gas chromatography. Unreacted perfluoroalkyl iodide ($R_fI$) is quantified using an external standard technique. The results are as follows: at 30 minutes 46.8 mole % $R_fI$ consumed, at 60 minutes 63.6 mole % $R_fI$ consumed, at 120 minutes 89.0 mole % $R_fI$ consumed, at 180 minutes 91.9 mole % $R_fI$ consumed and at 240 minutes only 92.7 mole % $R_fI$ consumed.

From the above results, it is obvious that the only process which results in high conversion for the addition of perfluoroalkyl iodides to olefins is that of the present invention. Lower conversions, i.e. <98%, such as are obtained by following the teachings of Haung, Journal of Fluorine Chemistry, 58, 1992, pp 1–8, would require a cumbersome and undesirable distillation to remove unreacted perfluoroalkyl iodides. Not only does the present invention achieve high levels of conversion, but it does so using only catalytic amounts of the free-radical initiator VAZO-67 and sulfite. Thus this process would produce far less waste in the effluent than one according to the teachings of Haung.

We claim:

1. A process for reacting a perfluoroalkyl iodide with a terminal olefinic compound, which comprises carrying out a free-radical addition reaction of the perfluoroalkyl iodide to the terminal olefinic group in the presence of 0.01 to 3 mole percent of an azoic compound as the free radical-generating initiator and 0.01 to 30 mole percent of an aqueous solution of a water-soluble salt selected from the group consisting of bisulfites and metabisulfites, both based on the perfluoroalkyl iodide.

2. A process according to claim 1, wherein the perfluoroalkyl group is one or more than one member of a homologous series of the formula $C_nF_{2n+1}$, wherein n is an integer from 4 to 20.

3. A process according to claim 1, wherein the water-soluble salt is a alkali metal or ammonium salt.

4. A process according to claim 3, wherein the water-soluble salt is a sodium or potassium salt.

5. A process according to claim 1, wherein the water-soluble salt is a sulfite or bisulfite salt.

6. A process according to claim 1, wherein the water-soluble salt is used in amounts ranging from 0.5 to 5 mol percent based on the perfluoroalkyl iodide.

7. A process according to claim 1, wherein the olefinic compound is unsubstituted or substituted by one or more than one functional groups, which may be the same or different, and are selected from hydroxy, carboxy, unsubstituted amino or amino which is mono- or disubstituted by $C_1$–$C_5$alkyl or hydroxy- or carboxy-substituted $C_1$–$C_5$alkyl, amide, $C_1$–$C_4$alkyl-substituted amide and anhydride groups.

8. A process according to claim 1, wherein the olefinic compound additionally contains one or more than one heteroatom-containing groups selected from ether, sulfide, sulfone, ester, amide and tertiary amino groups.

9. A process according to claim 1, wherein the olefinic compound is an unsaturated alcohol selected from allyl alcohol, methallyl alcohol, crotyl alcohol, 3-methyl-3-butene-1-ol, 1-butene-3-ol, 3-butene- 1-ol, dodecane- 1-ol- 11,12-ene, decane-1-ol-9,10-ene, trimethylolpropane diallylether, pentaerythritol mono-, di-, and triallylether, compounds of the formulae

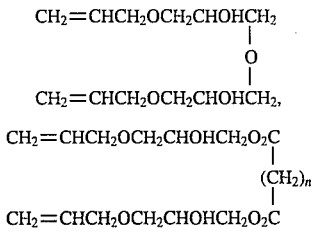

where n=1–4, $(CH_2=CHCH_2OCH_2)_2C(C_2H_5)CH_2OCH_2CH_2OH$, $(CH_2=CHCH_2OCH_2)_2CHOH$, $(CH_2=CHCH_2OCH_2)_2CHOCH_2CH_2OH$, $(CH_2=CHCH_2OCH_2CH(OH)CH_2)NR_2$, $(CH_2=CHCH_2OCH_2CH(OCH_2CH_2OH)CH_2)NR_2$, wherein $R_2$ is $C_1$–$C_5$alkyl or hydroxy- or carboxy-substituted $C_1$–$C_5$alkyl, $(CH_2=CHCH_2OCH_2CH(OH)CH_2)_2S$, $(CH_2=CHCH_2OCH_2CH(OCH_2CH_2OH)CH_2)_2S$, $(CH_2=CHCH_2OCH_2CHOH)_2$, oligomers of allyl glycidyl ether and adducts of allyl glycidyl ether with active hydrogen compounds selected from alcohols, amines and mercaptans.

10. A process according to claim 11, wherein the unsaturated olefin is selected from amino alcohols, amino acids, mercapto acids and mercapto alcohols.

11. A process according to claim 1, wherein the olefinic compound is an unsaturated acid selected from

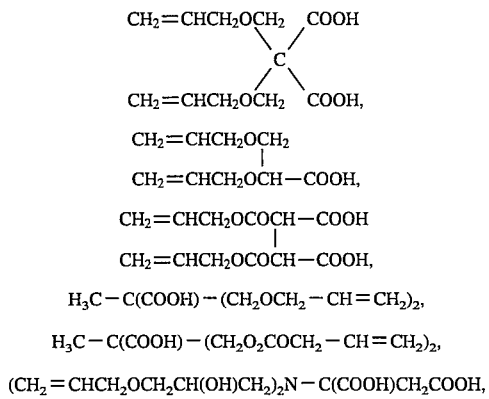

$H_3C-C(COOH)-(CH_2OCH_2-CH=CH_2)_2$, $H_3C-C(COOH)-(CH_2O_2COCH_2-CH=CH_2)_2$, $(CH_2=CHCH_2OCH_2CH(OH)CH_2)_2N-C(COOH)CH_2COOH$,

-continued $CH_2=CH-CH_2-NHCH(CO_2H)CH_2CH_2CH_2NH-CH_2-CH=CH_2$ and

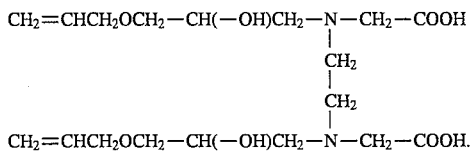

12. A process according to claim 1, wherein the olefinic compound is selected from 10-undecenoic acid, itaconic anhydride, allylsuccinic acid and its anhydride, hydroxybutyl vinyl ether, allyl glycidyl ether, and hydroxy- or carboxy-terminated 1,4- and 1,2-polybutadienes of 200 to 5000 molecular weight.

13. A process according to claim 1, wherein the olefinic compound is selected from allyl alcohol, pentaerythritol di- or triallyl ether, trimethylolpropane diallyl ether, glycerol-1,3-diallyl ether and 10-undecen-1-ol.

14. A process according to claim 1, wherein the olefinic compound is selected from allyl glycidyl ether, oligomers of allyl glycidyl ether, adducts of allyl glycidyl ether with amino acids and alcohols and mercapto acids and alcohols.

15. A process according to claim 1, which is carried out in the presence of a bisazo compound as a free radical-generating initiator.

16. A process according to claim 15, which is carried out in the presence of 0.5 to 2 mole percent of a bisazo compound, based on the perfluoroalkyl iodide, as the free radical-generating initiator.

17. A process according to claim 1, wherein the free radical-generating initiator is azobis-(isobutyronitrile), azobis(isovaleronitrile) or azobis(cyclohexane carbonitrile).

18. A process according to claim 1, which is carried out at a temperature of from about 50° to 120° C.

19. A process according to claim 1, which is carried out in the presence of an organic solvent which is selected from alcohols, ketones, esters, amides, hydrocarbons and mixtures thereof.

20. A process according to claim 19, wherein the organic solvent is methanol, ethanol, isopropanol, butanol, acetone, methyl ethyl ketone, methyl propyl ketone, isopropyl acetate, N-methylpyrrolidone, toluene or xylene or a mixture thereof.

21. A process according to claim 1, wherein the weight ratio of the aqueous solution of the water-soluble salt to the non-aqueous phase comprising the perfluoroalkyl iodide, the olefinic compound and any organic solvent employed, is from 0.05 to 10.

22. A process according to claim 21, wherein the weight ratio of the aqueous solution to the non-aqueous phase is from 0.1 to 0.5.

* * * * *